United States Patent
Rossen et al.

[11] Patent Number: 5,883,267
[45] Date of Patent: Mar. 16, 1999

[54] PROCESS FOR MAKING PHENYL HETEROCYCLES USEFUL AS COX-2 INHIBITORS

[75] Inventors: Kai Rossen, Westfield; Ralph P. Volante, Cranbury; Guo-Jie Ho, Scotch Plains; Roger N. Farr, Whitehouse Station; David J. Mathre, Skillman, all of N.J.

[73] Assignee: Merck & Co., Inc., Rahway, N.J.

[21] Appl. No.: 851,962

[22] Filed: May 6, 1997

Related U.S. Application Data

[60] Provisional application Nos. 60/018,644 May 31, 1996, 60/028,108 Oct. 9, 1996 and 60/028,109 Oct. 9, 1996.

[51] Int. Cl.⁶ .................................................. C07D 307/60
[52] U.S. Cl. .......................................................... 549/319
[58] Field of Search .............................................. 549/319

[56] References Cited

FOREIGN PATENT DOCUMENTS

| 754 687 | 1/1997 | European Pat. Off. . |
|---|---|---|
| WO 94/15932 | 7/1994 | WIPO . |
| WO 94/26731 | 11/1994 | WIPO . |
| WO 95/00501 | 1/1995 | WIPO . |
| WO 96/08482 | 3/1996 | WIPO . |
| WO 96/19469 | 6/1996 | WIPO . |
| 97/14691 | 4/1997 | WIPO . |

OTHER PUBLICATIONS

Handbook of Chemistry and Physics, 64th Ed., CRC Press, Inc. Boca Raton, Fl, P. C–375 and P. C–439, (1983).

*Primary Examiner*—Bernard Dentz
*Attorney, Agent, or Firm*—Richard C. Billups; D. L. Rose; Curtis C. Panzer

[57] ABSTRACT

The invention encompasses a process for making compounds of Formula I or Ia useful in the treatment of cyclooxygenase-2 mediated diseases.

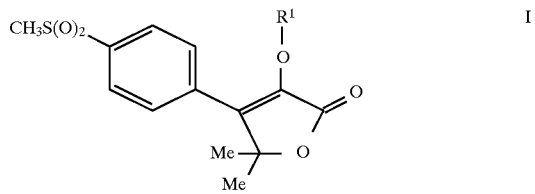

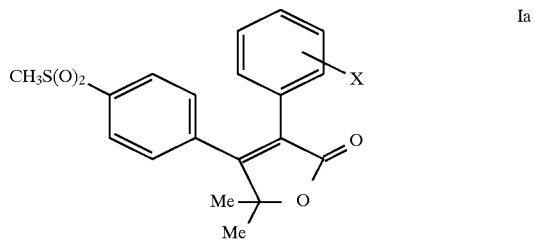

10 Claims, No Drawings

PROCESS FOR MAKING PHENYL HETEROCYCLES USEFUL AS COX-2 INHIBITORS

CROSS REFERENCE TO RELATED APPLICATIONS

This application is a non-provisional application based upon provisional application Ser. No. 60/018,644 filed on May 31, 1996, Ser. No. 60/028,108 filed on October 9, 1996 and Ser. No. 60/028,109 filed on Oct. 9, 1996, priority of which is claimed hereunder.

BACKGROUND OF THE INVENTION

This invention concerns a process for making certain anti-inflammatory compounds. In particular, the application concerns a process for making compounds of formulas I and Ia as disclosed hereinunder, which compounds are potent cyclooxygenase-2 inhibitors.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Up until recently, only one form of cyclooxygenase had been characterized, this corresponding to cyclooxygenase-1 or the constitutive enzyme, as originally identified in bovine seminal vesicles. Recently the gene for a second inducible form of cyclooxygenase (cyclooxygenase-2) has been cloned, sequenced and characterized from chicken, murine and human sources. This enzyme is distinct from the cyclooxygenase-1 which has now also been cloned, sequenced and characterized from sheep, murine and human sources. The second form of cyclooxygenase, cyclooxygenase-2, is rapidly and readily inducible by a number of agents including mitogens, endotoxin, hormones, cytokines and growth factors. As prostaglandins have both physiological and pathological roles, we have concluded that the constitutive enzyme, cyclooxygenase-1, is responsible, in large part, for endogenous basal release of prostaglandins and hence is important in their physiological functions such as the maintenance of gastrointestinal integrity and renal blood flow. In contrast, we have concluded that the inducible form, cyclooxygenase-2, is mainly responsible for the pathological effects of prostaglandins where rapid induction of the enzyme would occur in response to such agents as inflammatory agents, hormones, growth factors, and cytokines. Thus, a selective inhibitor of cyclooxygenase-2 will have similar antiinflammatory, antipyretic and analgesic properties to a conventional non-steroidal antiinflammatory drug, and in addition would inhibit hormone-induced uterine contractions and have potential anti-cancer effects, but will have a diminished ability to induce some of the mechanism-based side effects. In particular,such a compound should have a reduced potential for gastrointestinal toxicity, a reduced potential for renal side effects, a reduced effect on bleeding times and possibly a lessened ability to induce asthma attacks in aspirin-sensitive asthmatic subjects.

WO 94/15932 published Jul. 21, 1994 discloses a multi-step method of making bi-aryl furans via bi-aryl lactones, which method utilizes a keto-ester internal cyclization to the lactone. We have found that a significant amount of undesired by-products are produced by use of the disclosed process scheme, due to the external cyclization reactions which compete with the desired internal cyclization. While these by-products can be removed by suitable separation and purification techniques, we have sought to identify alternative processes to obviate the difficulties.

SUMMARY OF THE INVENTION

The invention encompasses a process for making compounds of Formula I and Formula Ia useful in the treatment of inflammation and other cyclooxygenase-2 mediated diseases.

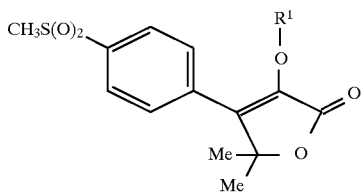

I

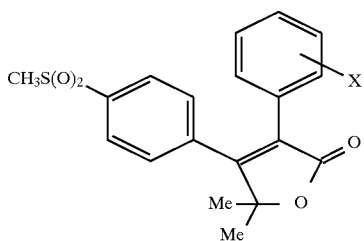

Ia

DETAILED DESCRIPTION OF THE INVENTION

In one aspect the invention encompasses a process for making compounds of Formula I useful in the treatment of inflammation and other cyclooxygenase-2 mediated diseases

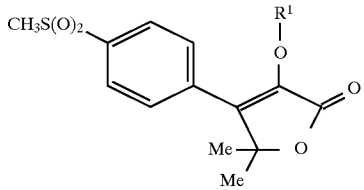

I $R^1$ is selected from the group consisting of
  (a) linear or branched $C_{1-6}$alkyl,
  (b) mono-, di- or tri-substituted phenyl or naphthyl wherein the substituents are selected from the group consisting of
    (1) hydrogen,
    (2) halo,
    (3) $C_{1-3}$alkoxy,
    (4) CN,
    (5) $C_{1-3}$ fluoroalkyl
    (6) $C_{1-3}$ alkyl,
    (7) —$CO_2H$, the process comprising:
  (a) reacting thioanisole

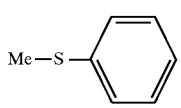

1 in a non-reactive solvent and in the presence of a Lewis Acid, with isobutyryl chloride

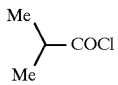

to yield compound 2

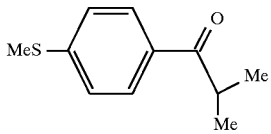

For purposes of this specification non-reactive solvents include halocarbon and polyhalocarbon solvents such as mono or di-halo $C_{1-4}$ alkyl including dichloromethane; aromatic solvents such as nitrobenzene, or halogenated aromatics and $C_{6-10}$ linear, branched or cyclic hydrocarbon solvent including hexane, cyclohexane or methylcyclohexane or $CS_2$. For this step, the non-reactive solvents are preferably cyclohexane or ortho dichlorobenzene. Suitable Lewis Acids include but are not limited to $AlCl_3$, $FeCl_3$, $TiCl_4$ and $SnCl_4$.

The molar ratio of thioanisole compound 1 to isobutyryl chloride may typically be varied from 1:1.5 to 1.5:1; preferably 1:1 to 1.5. Excess isobutyl chloride is typically used. Similarly, the molar ratio of compound of thioanisole compound 1 to Lewis Acid may typically be varied from 1:1.5 to 1.5:1. Preferably the molar ratio of thioanisole compound 1 to Lewis Acid is 1:1 to 1.5. The reaction step may conveniently be conducted at a temperature range of 0° to 25° C.; preferably 5° to 15° C. and is allowed to proceed until substantially complete in from 30 min. to 4 hours; typically 1 to 2 hours.

The reaction is preferably conducted is the absence of moisture, preferable under nitrogen.

(b) brominating reacting a compound 2 with brominating agent in a non-reactive solvent (as defined above), in the presence of a second solvent, such as ethyl acetate to yield compound

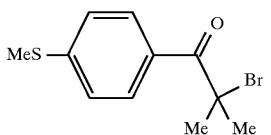

For purposes of this specification, brominating agent are intended to include $Br_2$, N-bromosuccinimide and dibromo dimethyl hydantoin. The bromine may be generated in situ. The second solvent is intended to include esters such as ethyl acetate, isopropyl acetate and tetrabutyl acetate and etheral solvents such as etheral solvents such as diethyl ether di-n-butyl and diisopropyl ethers, cyclic ethers such as tetrahydropyran, and tetrahydrofuran. Typically, molar ratio of compound 2 to brominating agent is approximately 1:1. Most often excess brominating agent is used. The reaction step may be conducted at a temperature range of 0° to 50° C.; preferably 5° to 20° C., and is allowed to proceed until substantially complete in from 30 minutes to 2 hours; typically 45 to 90 minutes.

In an alternative aspect, compound 2 may be chlorinated by the same procedure, rather than brominated. For purposes of this specification the chlorinating agents are intended to include $Cl_2$, N-chlorosuccinimide and dichloro dimethyl hydantoin.

(c) oxidizing compound 3 in a non-reactive solvent (as defined above), with an oxidizing agent, optionally in the presence of a suitable catalyst to yield compound 4

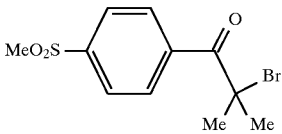

The oxidation may be accomplished by a number of means available in the art. See, for example Can. J. Chem. 59, 720 (1981), Can. J. Chem. 60, 618 (1982), J. Chem. Soc. (C) 1969, 233, J. Org. Chem., 28, 1140 (1963), Org. Prep. Proceed. Int, 13, 137 (1981), J. Org. Chem., 50, 1544, (1985), Chem. Ber., 119, 269, (1986), and Synthesis, 1015, 1987. We have found catalysed oxidation with hydrogen peroxide to be surprisingly superior in that undesired side-reaction oxidations are minimized and environmental impact and removal of side products are good, as water is the by product.

Suitable catalysts include sodium tungstate di-hydrate and tungstic acid.

Typically the molar ratio of compound 3 to oxidizing agent should be approximately 1 to 2:4, that is excess oxidizing agent is preferred. The reaction step may be conducted at a temperature range of 0° to 70° or 90° C.; preferably 10° to 65° or 75° C. and is allowed to proceed until substantially complete in from 1 to 5 hours; typically 2 to 4 hours.

(d) reacting compound 4 in an alkanol solvent with compound 5

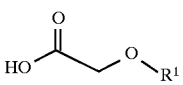

in the presence of a suitable base to yield a compound of formula 6

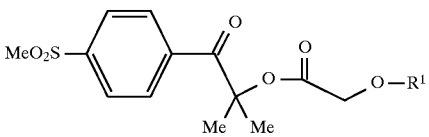

For purposes of this specification, the alkanol solvent includes, but is not limited to ethyl alcohol. For purposes of this specification, the suitable base is intended to include diisopropylethyl amine (DIEA). Typically the molar ratio of compound 4 to compound 5 may conviently be varied from 1.5:1 to 1:1.5; prefereably 1:1 to 1.2. Excess compound 5 is typically used. The ratio of compound 4 to suitable base is typically 1:1 to 2; preferably about 1:1.8. The reaction step a may be conducted at a temperature range of 0° to 80° C.; preferably 10° to 70° C., and is allowed to proceed until substantially complete in from 2 to 20 hours; typically 8 to 16 hours.

Isopropoxyacetic acid was prepared by addition of sodium chloroacetate to a solution of sodium isopropoxide in isopropanol, generated by reaction of sodium hydroxide and isopropanol. The reaction is typically complete after reflux for 4–5 h. The reaction is quenched by addition of water and isopropanol is removed under vacuum. The aqueous solution is acidified and saturated with sodium chloride and isopropoxyacetic acid is extracted into methyl t-butyl ether. Typically, the reaction yield is only moderate (~75%) due to hydrolysis. Regarding the preparation of Isopropoxyacetic acid, see also J. Chem. Soc.(c) 1969, 2698; J. Am. Chem. Soc. 1949, 71, 3372; and J. Chem Soc. Perkin. Trans. I 1983, 2479.

The penultimate ester 6 is formed by reaction of the bromosulfone and isopropoxyacetic acid, preferably in ethanol using DIPEA as the base. Side-products include the alcohol, olefin, and keto-alcohol shown immediately below, all of which can be effectively removed by crystallization of the ester from ethanol and the isolated yield is 70–78%.

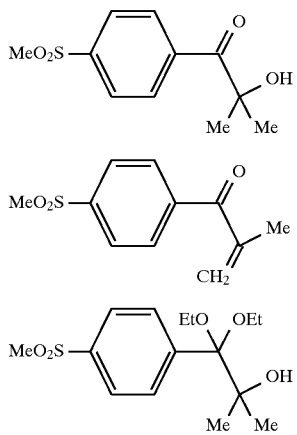

(e) reacting compound 6 in an aprotic solvent with a strong base to yield a cyclized compound of formula 7.

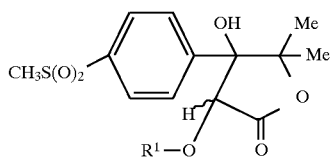

which after dehydration in the presence of a water scavenger yields a compound of formula I.

With regard to the cyclization, a strong base is required to prevent a cessation of the reaction after formation of the ester (6). Thus, for purposes of this specification the strong base shall be defined to include 1,8-Diazabicyclo[5.4.0]undec-7-ene (DBU), 1,4-diazabicyclo[2.2.2]octane (DABCO) and 1,5diazabicyclo[4.3.0]non-5-ene (DBN). For purposes of this specification the water scavenger shall be defined to include Esters of trifluoroacetic acid, such as isopropyl trifluoroacetate, esters of trichloroacetic acid and esters of alkyl or aryl sulfonic acid. Aprotic solvents shall be defined to include acetonitrile, N,N-dimethylformamide, methyl sulfoxide, propionitrile and nitromethane. Dehydration is accomplished by heating (refluxing). The molar ratio of ester to strong base typically about 1:1 to 1:2, with 1:1.5 preferred. The molar ratio of ester to water scavenger is typically 1:1 to 1:2, with 1:1.2 preferred. The reaction is allowed to proceed at 0° to 25° until substantially complete in 1 to 14 hours.

Bases such as potassium bis(trimethylsilyl)amide or Lithium diisopropylamide (LDA) cause the cleavage of the ester, possibly through ketene formation and are therefore less preferred. A significant amount of the above mentioned alcohol side product was formed together with several unidentified side-products, which were likely derived from the ketene. Cyclization under acidic conditions fail since ester cleavage is consistantly observed as the major reaction.

Ester 6 undergoes facile transesterification when the reaction is run in alcoholic solvents. Alcohol is formed in >60% in IPA and exclusively in EtOH. The reaction thus has to be carried out in aprotic solvents. Even in MeCN, ~40% of alcohol was formed at the end of reaction. The ester side product is rapidly hydrolyzed by the 1 equiv of water generated during the reacton. Therefore, an efficient water scavenger is important. Esters of trifluoroacetic acid were chosen because they would hydrolyze readily in the presence of DBU. Thus, addition of 1.2 equiv of ethyl trifluoroacetate reduced the formation of alcohol to ~5%. The reaction is advantageously carried out in a mixture of 1.2 equiv of isopropyl trifluoroacetate and 1.5 equiv of DBU (1 equiv needed to neutralize TFA) in acetonitrile at reflux. The reaction is typically complete in 14 h and the product crystallizes upon addition of water after partial removal of MeCN. The isolated yield is 94% (98% assay yield) with purity of >99 A % at 210 nm. The overall yield for esterification and cyclization is 65%.

SCHEME 1

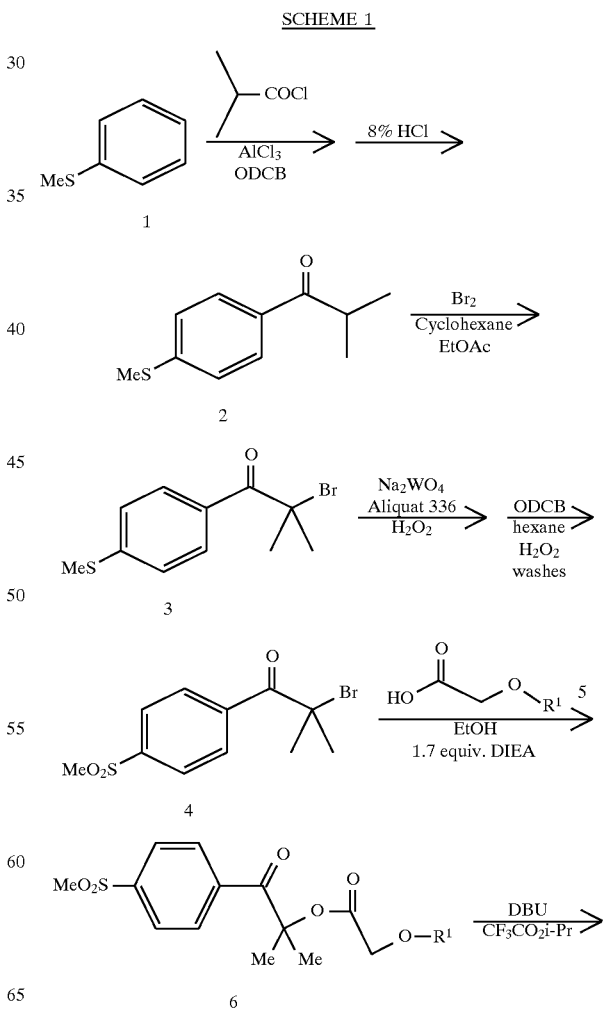

-continued
SCHEME 1

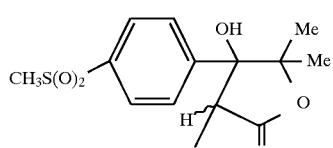

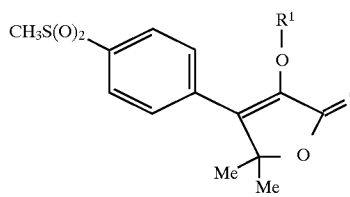

Scheme 1. Compounds of formula I are prepared in a 6 step process—3 steps starting from sodium chloroacetate, isopropanol, and the bromosulfone intermediate. Reaction of sodium chloroacetate with sodium isopropoxide gives isopropoxyacetic acid, which is coupled with the bromosulfone to form the ester. Cyclization and dehydration of the ester to form compounds of formula I is effected by a strong base in the presence of a water scavenger.

In an alternative procedure, compound 4 may be prepared as shown in Scheme 2 and Example 2.

SCHEME 2

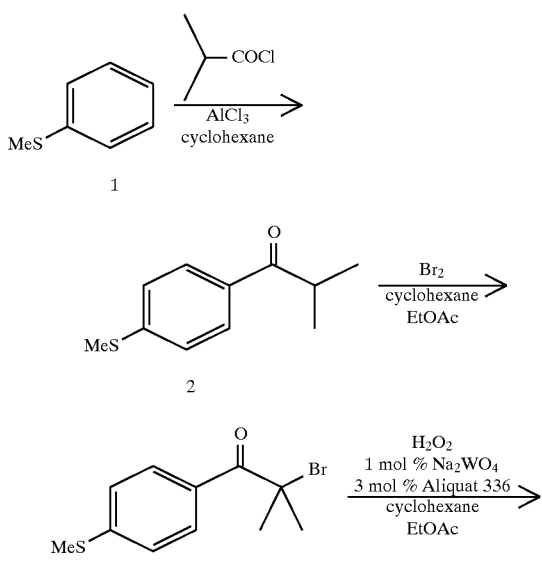

-continued
SCHEME 2

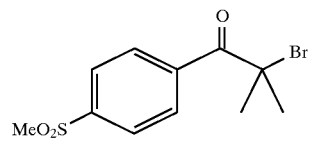

In a second aspect the invention encompasses a process for making compounds of Formula I useful in the treatment of inflammation and other cyclooxygenase-2 mediated diseases

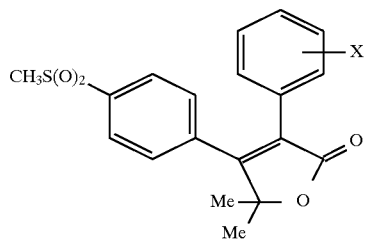

X is fluoro or chloro;
the process comprising:
(a) reacting thioanisole

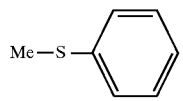

in a non-reactive solvent and in the presence of a Lewis Acid, with isobutyryl chloride

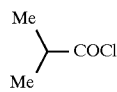

to yield compound 2

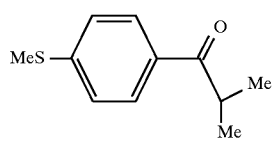

In an alternative embodiment, there may be more than one group "X" on the phenyl and X may be defined to include H, F and Cl.

For purposes of this specification non-reactive solvents include halocarbon and polyhalocarbon solvents such as mono or di-halo $C_{1-4}$ alkyl including dichloromethane; aromatic solvents such as nitrobenzene, or halogenated aromatics and $C_{6-10}$ linear, branched or cyclic hydrocarbon solvent including hexane, cyclohexane or methylcyclohexane or $CS_2$. For this step, the non-reactive solvents are preferably cyclohexane or ortho dichlorobenzene. Suitable Lewis Acids include but are not limited to $AlCl_3$, $FeCl_3$, $TiCl_4$ and $SnCl_4$.

The molar ratio of thioanisole compound 1 to isobutyryl chloride may typically be varied from 1:1.5 to 1.5:1; preferably 1:1 to 1.5. Excess isobutyl chloride is typically used. Similarly, the molar ratio of compound of thioanisole compound 1 to Lewis Acid may typically be varied from 1:1.5 to 1.5:1. Preferably the molar ratio of thioanisole compound 1 to Lewis Acid is 1:1 to 1.5. The reaction step may conveniently be conducted at a temperature range of 0° to 25° C.; preferably 5° to 15° C. and is allowed to proceed until substantially complete in from 30 min. to 4 hours; typically 1 to 2 hours.

The reaction is preferably conducted is the absence of moisture, preferable under nitrogen.

(b) brominating reacting a compound 2 with brominating agent in a non-reactive solvent (as defined above), in the presence of a second solvent, such as ethyl acetate to yield compound

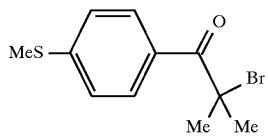
3

For purposes of this specification, brominating agent are intended to include $Br_2$, N-bromosuccinimide and dibromo dimethyl hydantoin. The bromine may be generated in situ. The second solvent is intended to include esters such as ethyl acetate, isopropyl acetate and tetrabutyl acetate and etheral solvents such as etheral solvents such as diethyl ether di-n-butyl and diisopropyl ethers, cyclic ethers such as tetrahydropyran, and tetrahydrofuran. Typically, molar ratio of compound 2 to brominating agent is approximately 1:1. Most often excess brominating agent is used. The reaction step may be conducted at a temperature range of 0° to 50° C.; preferably 5° to 20° C., and is allowed to proceed until substantially complete in from 30 minutes to 2 hours; typically 45 to 90 minutes.

In an alternative aspect, compound 2 may be chlorinated by the same procedure, rather than brominated. For purposes of this specification the chlorinating agents are intended to include $Cl_{12}$, N-chlorosuccinimide and dichloro dimethyl hydantoin.

(c) oxidizing compound 3 in a non-reactive solvent (as defined above), with an oxidizing agent, optionally in the presence of a suitable catalyst to yield compound 4

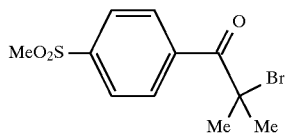
4

The oxidation may be accomplished by a number of means available in the art. See, for example *Can. J. Chem.* 59, 720 (1981), *Can. J. Chem.* 60, 618 (1982), *J. Chem. Soc.* (C) 1969, 233, *J. Org. Chem.*, 28, 1140 (1963), *Org. Prep. Proceed. Int*, 13, 137 (1981), *J. Org. Chem.*, 50, 1544, (1985), *Chem. Ber.*, 119, 269, (1986), and *Synthesis*, 1015, 1987. We have found catalysed oxidation with hydrogen peroxide to be surprisingly superior in that undesired side-reaction oxidations are minimized and environmental impact and removal of side products are good, as water is the by product.

Suitable catalysts include sodium tungstate di-hydrate and tungstic acid.

Typically the molar ratio of compound 3 to oxidizing agent should be approximately 1 to 2:4, that is excess oxidizing agent is preferred. The reaction step may be conducted at a temperature range of 0° to 70° or 90° C.; preferably 10° to 65° or 75° C. and is allowed to proceed until substantially complete in from 1 to 5 hours; typically 2 to 4 hours.

(d) reacting compound 4 in an alkanol solvent with compound 5a

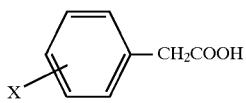
5a wherein X is F or Cl;

in the presence of a suitable base to yield a compound of

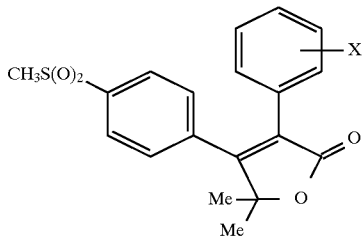
Ia

For purposes of this specification, the alkanol solvent includes, but is not limited to ethyl alcohol. For purposes of this specification, the suitable base is intended to include diisopropylethyl amine. Typically the molar ratio of compound 4 to compound 5a may conviently be varied from 1.5:1 to 1:1.5; prefereably 1:1 to 1.2. Excess compound 5a is typically used. The ratio of compound 4 to suitable base is typically 1:1 to 2; preferably about 1:1.8. The reaction step a may be conducted at a temperature range of 0° to 80° C.; preferably 10° to 70° C., and is allowed to proceed until substantially complete in from 2 to 20 hours; typically 8 to 16 hours.

We have found that in reaction step (d) at least a portion of the reactions react to produce, as an intermediate, the following epoxide A (wherein R is $C_{1-6}$alkyl):

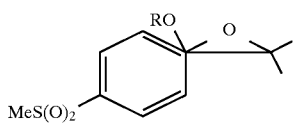
A

See JOC. 27, 4392 (1962); JACS. 76, 4402 (1954) and Chem. Ber. 116(11) 3631 (1983). Epoxide A is then converted to the compound of formula Ia by the reaction with a compound of formula 5a as described in step (d). Epoxide A may also be prepared by reacting a compound of formula 4 in a $C_{1-6}$alkanol solvent in the presence of a base such as $K_2CO_3$. Once again, see the references immediately above.

In an alternative aspect the compound of formula 3 and its chloro counterpart may be prepared by the following Friedel-Crafts reactions:

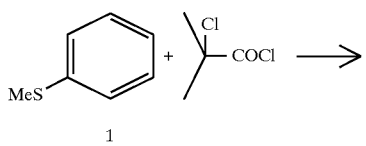

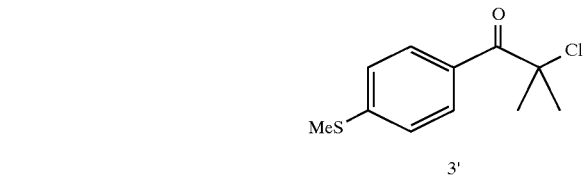
3'

-continued

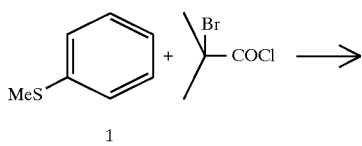

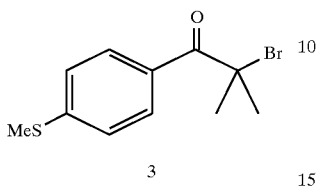

Scheme 1a

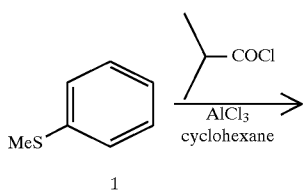

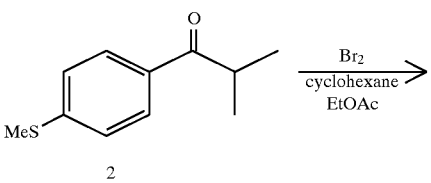

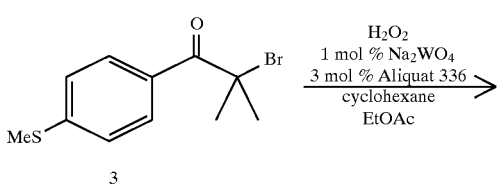

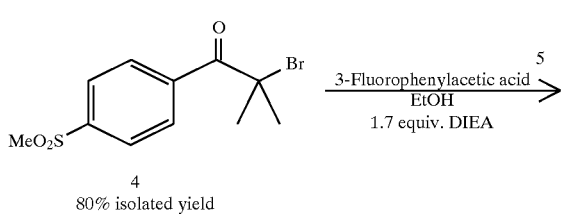

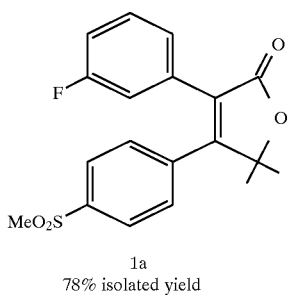

1a
78% isolated yield

One alternative set of conditions for preparing compound 4 is depicted in Scheme 2a and Example 4.

SCHEME 2A

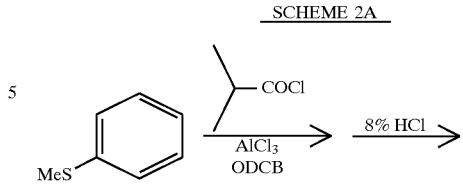

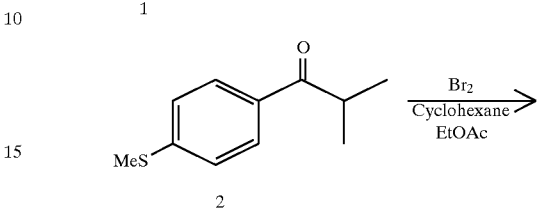

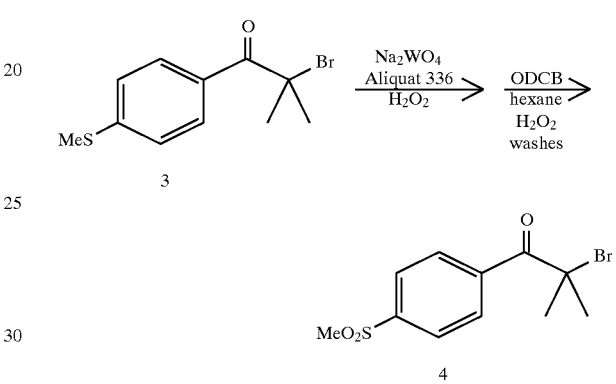

The Compound of Formula I and Ia is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis degenerative joint diseases (osteoarthritis), gout and ankylosing spondylitis, bursitis, burns, injuries, following surgical and dental procedures. In addition, such a compound may inhibit cellular neoplastic transformations and metastic tumor growth and hence can be used in the treatment of cancer. Compounds of formula I may also be useful for the treatment of dementia including pre-senile and senile dementia, and in particular, dementia associated with Alzheimer Disease (ie Alzheimer's dementia).

By virtue of its high cyclooxygenase-2 (COX-2) activity and/or its selectivity for cyclooxygenase-2 over cyclooxygenase-1 (COX-1) as defined above, compounds of formula I and formula Ia will prove useful as an alternative to conventional non-steroidal antiinflammatory drugs (NSAID'S) particularly where such non-steroidal antiinflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems (including those relating to reduced or impaired platelet function); kidney disease (eg impaired renal function); those prior to surgery or taking anticoagulants; and those susceptable to NSAID induced asthma.

Compounds of the present invention are inhibitors of cyclooxygenase-2 and are thereby useful in the treatment of cyclooxygenase-2 mediated diseases as enumerated above.

This activity is illustrated by their ability to selectively inhibit cyclooxygenase-2 over cyclooxygenase-1. Accordingly, in one assay, the ability of the compounds of this invention to treat cyclooxygenase mediated diseases can be demonstrated by measuring the amount of prostaglandin $E_2$ ($PGE_2$) synthesized in the presence of arachidonic acid, cyclooxygenase-1 or cyclooxygenase-2 and a compound of formula I and formula Ia. The IC50 values represent the concentration of inhibitor required to return $PGE_2$ synthesis to 50% of that obtained as compared to the uninhibited control. Illustrating this aspect, we have found that the Compounds of the Examples are more than 100 times more effective in inhibiting COX-2 than they are at inhibiting COX-1. In addition they all have a COX-2 IC50 of 1 nM to 1 $\mu$M. By way of comparison, Ibuprofen has an IC50 for COX-2 of 1 $\mu$M, and Indomethacin has an IC50 for COX-2 of approximately 100 nM.

For the treatment of any of these cyclooxygenase mediated diseases, compounds of formula I and formula Ia may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

The invention will now be illustrated by the following non-limiting examples in which, unless stated otherwise:

(i) all operations were carried out at room or ambient temperature, that is, at a temperature in the range 18°–25° C.; evaporation of solvent was carried out using a rotary evaporator under reduced pressure (600–4000 pascals: 4.5–30 mm. Hg) with a bath temperature of up to 60° C.; the course of reactions was followed by thin layer chromatography (TLC) or High Pressure Liquid Chromatography (HPLC) and reaction times are given for illustration only; melting points are uncorrected and 'd' indicates decomposition; the melting points given are those obtained for the materials prepared as described; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data; yields are given for illustration only; when given, NMR data is in the form of delta ($\delta$) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal; chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

The following abbreviations have the indicated meanings:

| Alkyl Group Abbreviations | | |
|---|---|---|
| Me | = | methyl |
| Et | = | ethyl |
| n-Pr | = | normal propyl |
| i-Pr | = | isopropyl |
| n-Bu | = | normal butyl |
| i-Bu | = | isobutyl |
| s-Bu | = | secondary butyl |
| t-Bu | = | tertiary butyl |
| c-Pr | = | cyclopropyl |
| c-Bu | = | cyclobutyl |
| c-Pen | = | cyclopentyl |
| c-Hex | = | cyclohexyl |

EXAMPLE 1

| 4-Thiomethyl-isobutyrophenone 2 | |
|---|---|
| Thioanisole 1 (MW = 124.2 d = 1.058) | 312 g (2.51 mol) |
| Isobutyryl chloride (MW = 106.55, d = 1.017) | 286 mL (2.61 mol) |
| Aluminum chloride (98%, MW = 133.34) | 345 g (2.59 mol) |
| ortho-dichlorobenzene | 1L |

A 5 L flask was charged under N2 with AlCl3 and ODCB. The vigorously stirred slurry was cooled to 8° C. and isobutyryl chloride was added over 30 min., keeping the temperature at 10°–15° C.

The addition of isobutyryl chloride was slightly exothermic.

The $AlCl_3$/isobutyryl chloride complex was aged at 7° C. for 30 min. Efficient cooling was applied and thioanisole 1 was added to the reaction mixture over 120 min., maintaining an internal temperature of 8°–13° C.

The addition of thioanisole was very exothermic. After the addition of about half of 1 a heavy yellow precipitate formed. The precipitation was accompanied by an exotherm. Gaseous HCl is formed in the reaction, so that the effluent gas stream should be scrubbed with aqueous NaOH before release into the atmosphere.

The reaction was warmed to 16° C. over 1 h.

The reaction mixture was a thick yellow slurry at this point. HPLC analysis of a quenched (EtOAc/$H_2O$) aliquot indicated completion of reaction.

The reaction mixture was cooled to 10° C. and 1.6 L of 5% aqueous HCl were added over 45 min.

The addition was extremely exothermic and especially the initial addition required careful temperature monitoring.

The biphasic mixture was vigorously stirred for 60 min. The lower organic phase was removed.

A quantitative assay of the organic phase indicated a 98% yield.

| 4-thiomethyl-α-bromoisobutyrophenone 3 | |
|---|---|
| 4-Thiomethyl-isobutyrophenone 2 in ODCB | 2.46 mol |
| Bromine (MW = 159.8, d – 3.102133 mL | (2.58 mol) |

A 5 L flask was charged with the solution of 2. Approximately 10% of the bromine were added and the reaction mixture was stirred until the red color had dissipated after 45 min. The remainder of the $Br_2$ was added over 60 min.

The reaction was exothermic and the temperature rose to ca. 32° C.

Gaseous HBr was released from the reaction, thus the effluent gas stream was scrubbed with aqueous NaOH before release into the atmosphere.

The reaction mixture was aged for 2 h at 30° C. when HPLC analysis indicated completion of the reaction Addition of a slight excess of Brs leads to the partial oxidation of the sulfide to the sulfoxide.

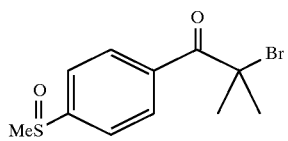

The reaction was quenched by the addition of 1.6 L $H_2O$ and the resulting 1820 mL of organic phase were used directly for the oxidation (95% assay yield).

| 4-Methylsulfonyl-α-bromoisobutyrophenone 4 | |
|---|---|
| 4-Thiomethyl-α-bromoisobutyrophenone 3 in ODCB | 990 mL solution, (ca. 1.27 mol) |
| Sodium tungstate dihdrate (MW = 329.86) | 4.50 g (0.014 mol) |
| Aliquat 336 (MW = 404) | 22 g (0.054 mol) |
| Hydrogen peroxide, 30% (MW = 34) | 390 mL (3.44 mol) |

To a solution of 3 in ODCB in a 2 L reaction vessel with heating jacket, reflux condenser and bottom valve was added under $N_2$ as solution of $Na_2WO_4$ and Aliquat 336 in 30 mL $H_2O$. The heterogeneous reaction mixture was heated with vigorous stirring to 35° C. and ca. 30 mL of $H_2O_2$ were added.

The oxidation was extremely exothermic. After an induction period of ca. 3 min. the temperature rose quickly to 50°–65° C.

The remainder of the $H_2O_2$ was added over 1 h. At the end of the addition HPLC analysis indicated completion of the reaction.

The reaction mixture was heated to 80° C., the lower organic phase was removed and cooled to 6° C. over 1 h.

The product precipitated at ca. 50° C. without seeding.

The slurry was filtered and washed with 250 mL of ODCB and 300 mL of hexane and three times with 200 mL of 60° C. $H_2O$. After drying 378 g of 4 (97% yield, ca. 91% overall yield from thioanisole) were obtained as a white powder.

| Preparation of isopropoxyacetic acid | | | |
|---|---|---|---|
| | amount | mol | equiv |
| Material | | | |
| Sodium chloroacetate (98%) | 159 g | 1.34 | 1.00 |
| Sodium hydroxide (97%) | 60 g | 1.45 | 1.08 |
| Isopropanol | 6 L | | |
| Conc. hydrochloric acid (~12.1 M) | 125 mL | 1.50 | 1.12 |
| Sodium Chloride | ~90 g | | |
| t-butylmethyl ether (MTBE) | 2.5 L | | |
| Toluene | 0.6 L | | |
| Product | | | |
| Isopropoxyacetic acid | 158 g | 1.34 | 1.00 |

A 5-L vessel fitted with a mechanical stirrer, thermocouple probe, and nitrogen inlet is charged with 2.0 L of isopropanol (K.F. 220 μg/mL) and sodium hydroxide (60 g, 1.45 mol). The mixture was heated at reflux until the solid sodium hydroxide dissolved.

A homogeneous solution is resulted after reflux for 3 h.

The solution was cooled at ~70° C. and toluene (150 mL) was added. It was distilled until ~1 L of distillate was collected. A mixture of IPA/toluene (85:15, 1 L) was added and ~1 L of liquid was distilled off (repeated 3x). At the end of distillation (~4 L of distillate collected), the solution was diluted with IPA to a volume of ~3.0 L.

The distillate is assayed to determine the amount of water removed. If the water removed is <75% of the theoretical amount (K.F. of IPA+that in NaOH+1 equiv generated), the distillation should be continued. The solution was then cooled at 60°–70° C. and sodium chloroacetate (159 g, 1.34 mol) was added in portions over 5 min. No exotherm is observed during the addition.

The mixture was heated at reflux for 3 h and a sample of the slurry was taken for assay.

The reaction is followed by $^1$HNMR. An aliquot (~0.2 mL) of the mixture is taken and evaporated to dryness. The residue is dissolved in $D_2O$ for $^1$HNMR measurement. The reaction is considered completed whenthe starting material is <3% vs. product.

| | |
|---|---|
| δ 3.82 (s), i-PrO—$CH_2$—$CO_2$- | product |
| δ 4.03 (s), Cl—$CH_2$—$CO_2$- | starting material |
| δ 3.90 (s), HO—$CH_2CO_2$- | hydrolysis product |

The reaction was quenched by addition of 600 mL of water and concentrated under reduced pressure (150–200 mBar, 50°–60° C.) until ~2.5 L of distillated was collected. More water was added (400 mL) and the solution was distilled at normal pressure until the batch temperature reached ~103° C. (~1 L of solution left, ~3 L of solvent removed). The solution was cooled at 10°–20° C. and neutralized by addition of conc. hydrochloric acid (125 mL, 1.5 mol).

External cooling may be needed during the addition of acid. The final pH should be >2.3, preferably ~2.

MTBE (800 mL) was added. The aqueous solution was saturated with sodium chloride (~90 g) and the two-phase mixture was agitated for 0.5 h at 10°–15° C. The layers were separated and the aqueous layer was back extracted with 2×600 mL of MTBE. The organic layers were combined and washed with 2×100 mL of saturated aqueous sodium chloride.

The pH of the 2nd brine wash should be >2.5.

The solution was dried over 4A molecular sieves (100 g) for 14 h and filtered. The sieves were washed with 3×150 mL of MTBE. MTBE was removed under reduced pressure (~200 mBar, 45°–50° C.). Isopropoxyacetic acid was obtained as a slightly yellow liquid.

Yield: 118 g, 75% yield corrected for remaining MTBE ($^1$NNMR).

Esterification

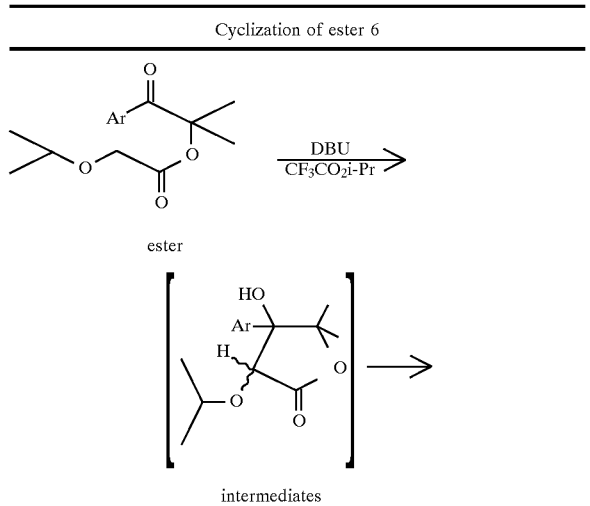

| Material | amount | mol | equiv |
|---|---|---|---|
| Bromosulfone | 50.0 g | .16 | 1.00 |
| Isopropoxyacetic acid | 23.2 g | .20 | 1.20 |
| Diisopropylethylamine | 48.5 mL | .28 | 1.70 |
| Ethanol (200 proof) | 450 mL | | |
| Product | | | |
| Ester | 56.0 g | .16 | 1.00 |

A 1 L flask fitted with a mechanical stirrer, nitrogen inlet, and thermocouple was sequentially charged with dry ethanol (450 mL, K.F.<100 µg/mL), isopropoxyacetic acid (23.2 g), diisopropylethylamine (48.5 mL) and the bromosulfone (50.0 g). The mixture is heated to reflux until the bromosulfone is not detected (HPLC, reaction time 12–14 hours).

The reaction is considered complete when the bromosulfone is <0.05 A % vs. product.

After the reaction was complete, the solution was allowed to cool and seeded at 42° C. Crystallization initiated immediately and the mixture was cooled to 1° C. and aged 1 hr. The product ester is filtered and washed with ethanol (0° C. 50 mL wash). After drying in a vacuum oven, the white crystalline material was used as is in the next step.

Yield: 41.5 g, 74%. Purity: 99 A % at 210 nm. ML losses are typically 4–6%.

Cyclization of ester 6

| Material | amount | mol | equiv |
|---|---|---|---|
| Ester | 5500 g | 16.1 | 1.00 |
| DBU | 3670 g | 24.1 | 1.50 |
| Isopropyl trifluoroacetate | 3010 g | 19.3 | 1.20 |
| Acetonitrile | 35 L | | |
| Water | 60 L | | |
| Product | | | |
| Ia | 5220 g | 16.1 | 1.00 |

A 100-L vessel fitted with a mechanical stirrer, nitrogen inlet, and thermocouple was sequentially charged with dry acetonitrile (32.2 L, K.F.<100 µg/mL), isopropyl trifluoroacetate (3010 g, 19.3 mol), and DBU (3670 g, 24.1 mol). The solution was stirred at ~20° C. for 15 min and the ester (5500 g, 16.1 mol) was added. The solution was heated at reflux under nitrogen and the progress of the reaction was followed by HPLC.

The reaction is considered complete when the intermediate peaks are <0.2 A % vs. product.

After the reaction was complete, the solution was cooled at ~40° C. and filtered (1µ in-line capsule). The solution was then concentrated at 40°–50° C. under reduced pressure until 20 L of distillate was collected. Water (35 L) was added slowly at ~45° C. After ~13 L of water was added, the solution turned cloudy (40°–45° C.) and ~2 g of crystalline Ia was added as the seed. The mixture was aged for 30 min and the remaining water was added. The mixture was aged at ~20° C. for 6 h then filtered. The cake was washed with 2×6.5 L of 1:4 MeCN/water and 3×6.5 L of water. The product was air dried and dried in vacuo (35° C., 200 mBar).

Yield: ~4800 g, 92%. Purity: >99.9 LCAP at 210 nm. TG: 0.1%.

EXAMPLE 2

(Alternative Preparation Of Compound 4)

| 4-Thiomethoxy-isobutyrophenone 2 | |
|---|---|
| Thioanisole 1 (MW = 124.2, d = 1.058) | 2.34 Kg (18.86 mol) |
| Isobutyryl chloride (MW = 106.55, d = 1.017) | 2.421 Kg (22.73 mol) |
| Aluminum chloride (98%, MW = 133.34) | 3.03 Kg (22.73 mol) |
| Cyclohexane | 20 L |

A 100 L reactor with internal cooling/heating coils and bottom release valve was charged under $N_2$ with $AlCl_3$ and cyclohexane. The vigorously stirred slurry was cooled to 7° C. and isobutyryl chloride was added over 30 min., keeping the temperature at 7°–12° C.

The addition of isobutyryl chloride was slightly exothermic and led to the formation of a clear solution.

The AlCl$_3$/isobutyryl chloride complex was aged at 10° C. for 30 min. Efficient cooling was applied and thioanisole 1 was added to the reaction mixture over 30 min., maintaining the internal temperature of 8°–12° C.

The addition of thioanisole was very exothermic and led to the formation of a deeply yellow slurry. The acylation was accompanied by the release of gaseous HCl, so that the effluent gas stream was scrubbed with aqueous NaOH before release into the atmosphere. The reaction did not proceed at an appreciable rate at temperatures below ca. 5° C.

The reaction was warmed to 19° C. over 2 h and was then aged for an additional 2 h at 22° C.

The reaction mixture was a thick yellow slurry at this point HPLC analysis of a quenched (EtOAc/H$_2$O) aliquot indicated completion of reaction.

The reaction mixture was cooled to 10° C. and 8 L of H$_2$O was added over 45 min.

The addition was extremely exothermic and especially the initial addition required careful temperature monitoring.

To the reaction vessel were added 32 L of EtOAc and the reaction mixture was stirred for 30 min. The aqueous phase was removed and the organic phase was washed twice with 8 L of ca. 1N aqueous HCl and once with 8 L of H$_2$O. The organic solution was dried over Na$_2$SO$_4$ for the next reaction.

| 4-Thiomethoxy-α-bromobutyrophenone 3 | |
|---|---|
| 4-Thiomethoxy-butyrophenone 2 in 32 L of cyclohexane and 32 L of EtOAc | ca. 31 mol |
| Bromine (MW = 159.8, d = 3.102) | 5.20 Kg (32.5 mol) |

A 100 L reactor with internal cooling/heating coils and bottom valve was charged with the solution of 2. Bromine was added slowly over 90 min. to the solution.

The reaction was exothermic and the temperature rose to a. 35° C. The bromination was very slow at temperatures below 15° C.

Gaseous HBr was released from the reaction, thus the effluent gas stream was scrubbed with aqueous NaOH before release into the atmosphere.

It was not necessary to dry the EtOAc/cyclohexane solution of 2 prior to the bromination. It was found that the formation of 3 in a H$_2$O saturated system proceeded equally well, and that excess Br$_2$ oxidized the sulfide to the sulfoxide.

At the end of the addition, HPLC analysis indicated completion of the reaction.

The reaction mixture was washed with 15 L of H$_2$O, 8 L of saturated aqueous NaHCO$_3$ solution and twice with 4 L of H$_2$O.

| 4-Methylsulfonyl-α-bromoisobutyrophenone 4 | |
|---|---|
| 4-Thiomethoxy-α-bromobutyrophenone 3 in ca. 16 L of cyclohexane and 16 L of EtOAc | ca. 15.5 mol |
| Sodium tungstate dihydrate (MW = 329.86) | 51 g (0.155 mol) |
| Aliquat 336 (MW = 404) | 190 g (0.47 mol) |
| Hydrogen peroxide, 30% (MW = 34) | 4.8 L (42.5 mol) |

To a solution of 3 in EtOAc and cyclohexane in a 100 L reaction vessel with internal heating/cooling coils, double reflux condensers and bottom valve was added under N$_2$ 2 L of H$_2$O, Na$_2$WO$_4$ and Aliquat 336. The heterogeneous reaction mixture was heated with vigorous stirring to 59° C. and ca. 300 mL of H$_2$O$_2$ were added.

The oxidation was extremely exothermic. After an induction period of ca. 3 min. the temperature rose quickly to 65° C., at which point reflux began.

The remainder of the H$_2$O$_2$ was added over 1 h at a rate that maintained a gentle reflux. At the end of the addition the reaction mixture was aged at 62° C. for 1 h, when HPLC analysis indicated completion of the reaction.

The aqueous phase was removed at 62° C. and the organic phase was washed twice at 62° C. with 4 L H$_2$O. At atmospheric pressure, 5 L of solvent were removed by distillation from the solution.

The internal temperature rose to 75° C. during the distillation. The distillation azeotropically dried the solution, and thus simplified the drying of the isolated 4.

The solution was cooled to 10° C. over 3 h.

The product precipitated at ca. 50° C. without seeding.

The slurry was filtered and washed with 8 L of EtOAc/cyclohexane 50/50 and 8 L of cyclohexane. After drying in a N$_2$ stream, 3.79 Kg of 4 were obtained as a white powder.

Processing of an equal size batch using the same conditions gave 3.75 Kg of 4.

EXAMPLE 3

| 4-Thiomethoxy-isobutyrophenone 2 | |
|---|---|
| Thioanisole 1 (MW = 124.2, d = 1.058) | 2.34 Kg (18.86 mol) |
| Isobutyryl chloride (MW = 106.55, d = 1.017) | 2.421 Kg (22.73 mol) |
| Aluminum chloride (98%, MW = 133.34) | 3.03 Kg (22.73 mol) |
| Cyclohexane | 20 L |

A 100 L reactor with internal cooling/heating coils and bottom release valve was charged under N$_2$ with AlCl$_3$ and cyclohexane. The vigorously stirred slurry was cooled to 7° C. and isobutyryl chloride was added over 30 min., keeping the temperature at 7°–12° C.

The addition of isobutyryl chloride was slightly exothermic and led to the formation of a clear solution.

The AlCl$_3$/isobutyryl chloride complex was aged at 10° C. for 30 min. Efficient cooling was applied and thioanisole 1 was added to the reaction mixture over 30 min., maintaining the internal temperature of 8°–12° C.

The addition of thioanisole was very exothermic and led to the formation of a deeply yellow slurry. The acylation was accompanied by the release of gaseous HCl, so that the effluent gas stream was scrubbed with aqueous NaOH before release into the atmosphere. The reaction did not proceed at an appreciable rate at temperatures below ca. 5° C.

The reaction was warmed to 19° C. over 2 h and was then aged for an additional 2 h at 22° C.

The reaction mixture was a thick yellow slurry at this point HPLC analysis of a quenched (EtOAc/H$_2$O) aliquot indicated completion of reaction.

The reaction mixture was cooled to 10° C. and 8 L of H$_2$O was added over 45 min.

The addition was extremely exothermic and especially the initial addition required careful temperature monitoring.

To the reaction vessel were added 32 L of EtOAc and the reaction mixture was stirred for 30 min. The aqueous phase was removed and the organic phase was washed twice with 8 L of ca. 1N aqueous HCl and once with 8 L of H$_2$O. The organic solution was dried over Na$_2$SO$_4$ for the next reaction.

| 4-Thiomethoxy-α-bromobutyrophenone 3 | |
| --- | --- |
| 4-Thiomethoxy-butyrophenone 2 in 32 L of cyclohexane and 32 L of EtOAc | ca. 31 mol |
| Bromine (MW = 159.8, d = 3.102) | 5.20 Kg (32.5 mol) |

A 100 L reactor with internal cooling/eating coils and bottom valve was charged with the solution of 2. Bromine was added slowly over 90 min. to the solution.

The reaction was exothermic and the temperature rose to a. 35° C. The bromination was very slow at temperatures below 15° C.

Gaseous HBr was released from the reaction, thus the effluent gas stream was scrubbed with aqueous NaOH before release into the atmosphere.

It was not necessary to dry the EtOAc/cyclohexane solution of 2 prior to the bromination. It was found that the formation of 3 in a $H_2O$ saturated system proceeded equally well, and that excess $Br_2$ oxidized the sulfide to the sulfoxide.

At the end of the addition, HPLC analysis indicated completion of the reaction.

The reaction mixture was washed with 15 L of $H_2O$, 8 L of saturated aqueous $NaHCO_3$ solution and twice with 4 L of $H_2O$.

| 4-Methylsulfonyl-α-bromoisobutyrophenone 4 | |
| --- | --- |
| 4-Thiomethoxy-α-bromobutyrophenone 3 in ca. 16 L of cyclohexane and 16 L of EtOAc | ca. 15.5 mol |
| Sodium tungstate dihydrate (MW = 329.86) | 51 g (0.155 mol) |
| Aliquat 336 (MW = 404) | 190 g (0.47 mol) |
| Hydrogen peroxide, 30% (MW = 34) | 4.8 L (42.5 mol) |

To a solution of 3 in EtOAc and cyclohexane in a 100 L reaction vessel with internal heating/cooling coils, double reflux condensers and bottom valve was added under $N_2$ 2 L of $H_2O$, $Na_2WO_4$ and Aliquat 336. The heterogeneous reaction mixture was heated with vigorous stirring to 59° C. and ca. 300 mL of $H_2O_2$ were added.

The oxidation was extremely exothermic. After an induction period of ca. 3 min. the temperature rose quickly to 65° C., at which point reflux began.

The remainder of the $H_2O_2$ was added over 1 h at a rate that maintained a gentle reflux. At the end of the addition the reaction mixture was aged at 62° C. for 1 h, when HPLC analysis indicated completion of the reaction.

The aqueous phase was removed at 62° C. and the organic phase was washed twice at 62° C. with 4 L $H_2O$. At atmospheric pressure, 5 L of solvent were removed by distillation from the solution.

The internal temperature rose to 75° C. during the distillation. The distillation azeotropically dried the solution, and thus simplified the drying of the isolated 4.

The solution was cooled to 10° C. over 3 h.

The product precipitated at ca. 50° C. without seeding.

The slurry was filtered and washed with 8 L of EtOAc/cyclohexane 50/50 and 8 L of cyclohexane. After drying in a $N_2$ stream, 3.79 Kg of 4 were obtained as a white powder.

Processing of an equal size batch using the same conditions gave 3.75 Kg of 4.

| Compound 1a | |
| --- | --- |
| 4-Methylsulfonyl-α-bromoisobutyrophenone 4 (MW = 305.2) | 3.63 Kg (11.9 mol) |
| 3-Fluorophenylacetic acid (MW = 154.1) 5a | 2.02 Kg (13.1 mol) |
| Diisopropylethylamine (MW = 129.2, d = 0.742) | 3.52 L (20.2 mol) |
| Ethanol, punctilious 200 proof | 24 L |

A 50 L flask under $N_2$ was charged with 4 and 5a. The EtOH and the DIEA were added at 22° C. and the resulting slurry was heated to 72° C. for 16 h.

The reaction turned homogeneous at 60° C. During the course of the reaction Compound la precipitated from the reaction mixture.

HPLC analysis of the supernatant indicated completion of the reaction.

The solution was heated at reflux for 1 h and 1.2 L of $H_2O$ were added over 30 min. The slurry was then cooled to 15° C. over 6 h, filtered and washed with 8 L of EtOH/$H_2O$ 95/5, 8 L of EtOH/$H_2O$ 50/50 and 8 L of punctilious EtOH. The resulting white crystalline product was dried in a $N_2$ stream to give 3.34 Kg of Compound 1a (78% yield).

EXAMPLE 4

| 4-Thiomethyl-isobutyrophenone 2 | |
| --- | --- |
| Thioanisole 1 (MW = 124.2 d = 1.058) | 312 g (2.51 mol) |
| Isobutyryl chloride (MW = 106.55, d = 1.017) | 286 mL (2.61 mol) |
| Aluminum chloride (98%, MW = 133.34) | 345 g (2.59 mol) |
| ortho-dichlorobenzene | 1 L |

A 5 L flask was charged under N2 with AlCl3 and ODCB. The vigorously stirred slurry was cooled to 8° C. and isobutyryl chloride was added over 30 min., keeping the temperature at 10°–15° C.

The addition of isobutyryl chloride was slightly exothermic.

The $AlCl_3$/isobutyryl chloride complex was aged at 7° C. for 30 min. Efficient cooling was applied and thioanisole 1 was added to the reaction mixture over 120 min., maintaining an internal temperature of 8°–13° C.

The addition of thioanisole was very exothermic. After the addition of about half of 1 a heavy yellow precipitate formed. The precipitation was accompanied by an exotherm. Gaseous HCl is formed in the reaction, so that the effluent gas stream should be scrubbed with aqueous NaOH before release into the atmosphere.

The reaction was warmed to 16° C. over 1h.

The reaction mixture was a thick yellow slurry at this point. HPLC analysis of a quenched (EtOAc/$H_2O$) aliquot indicated completion of reaction.

The reaction mixture was cooled to 10° C. and 1.6 L of 5% aqueous HCl were added over 45 min.

The addition was extremely exothermic and especially the initial addition required careful temperature monitoring.

The biphasic mixture was vigorously stirred for 60 min. the lower organic phase was removed.

A quantitative assay of the organic phase indicated a 98% yield.

| 4-thiomethyl-α-bromoisobutyrophenone 3 | |
|---|---|
| 4-Thiomethyl-isobutyrophenone 2 in ODCB | 2.46 mol |
| Bromine (MW = 159.8, d – 3.102133 mL (2.58 mol) | |

A 5 L flask was charged with the solution of 2. Approximately 10% of the bromine were added and the reaction mixture was stirred until the red color had dissipated after 45 min. The remainder of the Br₂ was added over 60 min.

The reaction was exothermic and the temperature rose to ca. 32° C.

Gaseous HBr was released from the reaction, thus the effluent gas stream was scrubbed with aqueous NaOH before release into the atmosphere.

The reaction mixture was aged for 2 h at 30° C. when HPLC analysis indicated completion of the reaction Addition of a slight excess of Br₂ leads to the partial oxidation of the sulfide to the sulfoxide 8.

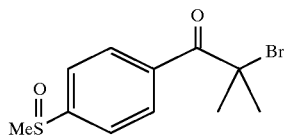

The reaction was quenched by the addition of 1.6 L H₂O and the resulting 1820 mL of organic phase were used directly for the oxidation (95% assay yield).

| 4-Methylsulfonyl-α-bromoisobutyrophenone 4 | |
|---|---|
| 4-Thiomethyl-α-bromoisobutyrophenone 3 | 990 mL solution, (ca. 1.27 in ODCB mol) |
| Sodium tungstate dihdrate (MW = 329.86) | 4.50 g (0.014 mol) |
| Aliquat 336 (MW = 404) | 22 g (0.054 mol) |
| Hydrogen peroxide, 30% (MW = 34) | 390 mL (3.44 mol) |

To a solution of 3 in ODCB in a 2 L reaction vessel with heating jacket, reflux condenser and bottom valve was added under N₂ as solution of Na₂WO₄ and Aliquat 336 in 30 mL H₂O. The heterogeneous reaction mixture was heated with vigorous stirring to 35° C. and ca. 30 mL of H₂O₂ were added.

The oxidation was extremely exothermic. After an induction period of ca. 3 min. the temperature rose quickly to 50°–65° C.

The remainder of the H₂O₂ was added over 1 h. At the end of the addition HPLC analysis indicated completion of the reaction.

The reaction mixture was heated to 80° C., the lower organic phase was removed and cooled to 6° C. over 1 h.

The product precipitated at ca. 50° C. without seeding.

The slurry was filtered and washed with 250 mL of ODCB and 300 mL of hexane and three times with 200 mL of 60° C. H₂O. After drying 378 g of 4 (97% yield, ca. 91% overall yield from thioanisole) were obtained as a white powder.

| Compound 1a | |
|---|---|
| 4-Methylsulfonyl-α-bromoisobutyrophenone 4 (MW = 305.2) | 28.37 g (0.093 mol) |
| 3-Fluorophenylacetic acid (MW = 154.1) 5a | 15.8 g (0.102 mol) |
| Diisopropylethylamine (MW = 129.2, d = 0.742) | 28 mL (0.16 mol) |
| Ethanol, 2BAT | 160 mL |

A 500 mL flask under N₂ was charged with 4 and 5a. The EtOH and the DIEA were added at 22° C. and the resulting slurry was heated at 76° C. for 14 h.

The reaction turned homogeneous at 60° C. and the product precipitated during the age.

The slurry was cooled to 25° C. over 4 h, filtered and washed with 150 mL of 2BAT EtOH. The resulting white crystalline product was dried in a N₂ stream to give 25.02 g of Compound 1a (75% yield).

EXAMPLE 5

Compound A (R=ethyl)

To a solution of 4-methylsulfonyl-α-bromo isobutyrophenone (814 mg, 2.67 mmol) in 13 ml of ethanol is added 2.54 g of solid K₂CO₃. The reaction mixture is filtered after 3 hours and the organic filtrate is evaporated to give 744 mg of compound A (R=ethyl) as a clear oil.

¹H NMR (CDCl₃) 7.9 (2H, d), 7.5 (2H, d), 3.9 (1H, dt), 3.2 (1H,), 2.5 (3H, s), 1.5 (3H, s), 1.0 (3H, t), 0.8 (3H, s).

What is claimed:

1. A process for making compounds of Formula I

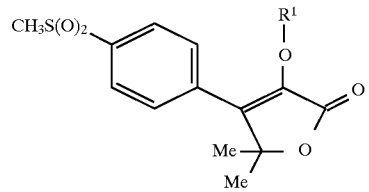

wherein:

R¹ is selected from the group consisting of
(a) linear or branched C₁₋₆alkyl,
(b) mono-, di- or tri-substituted phenyl or naphthyl wherein the substituents are selected from the group consisting of
(1) hydrogen,
(2) halo,
(3) C₁₋₃alkoxy,
(4) CN,
(5) C₁₋₃ fluoroalkyl
(6) C₁₋₃ alkyl,
(7) —CO₂H, the process comprising:

(a) reacting thioanisole:

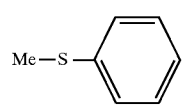

in a non-reactive solvent and in the presence of a Lewis Acid, with isobutyryl chloride:

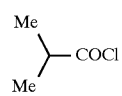

to yield compound 2:

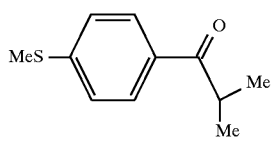

(b) brominating compound 2 with a brominating agent in a non-reactive solvent in the presence of a second solvent to yield compound 3:

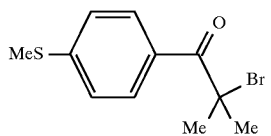

(c) oxidizing compound 3 in a non-reactive solvent with an oxidizing agent, optionally in the presence of a suitable catalyst to yield compound 4:

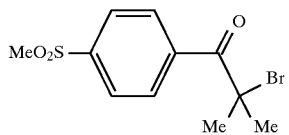

(d) reacting compound 4 in an alkanol solvent with compound 5:

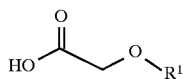

in the presence of a suitable base to yield a compound of formula 6:

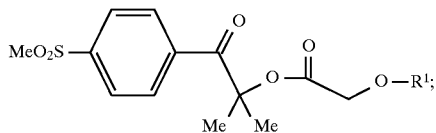

(e) reacting compound 6 in an aprotic solvent with a strong base to yield a cyclized compound of formula 7:

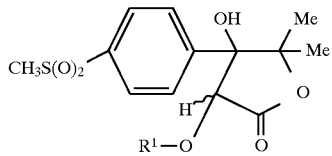

which after dehydration in the presence of a water scavenger yields a compound of formula I.

2. A process for making compounds of Formula I:

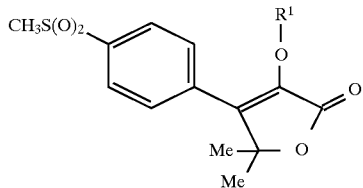

wherein:
R$^1$ is selected from the group consisting of:
(a) linear or branched $C_{1-6}$alkyl,
(b) mono-, di- or tri-substituted phenyl or naphthyl wherein the substituents are selected from the group consisting of
  (1) hydrogen,
  (2) halo,
  (3) $C_{1-3}$alkoxy,
  (4) CN,
  (5) $C_{1-3}$ fluoroalkyl
  (6) $C_{1-3}$ alkyl,
  (7) —CO$_2$H,
comprising the steps of:
(e) reacting compound 6:

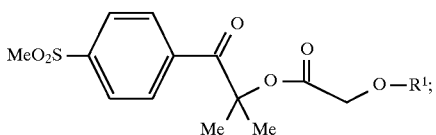

in an aprotic solvent with a strong base to yield a cyclized compound of formula 7:

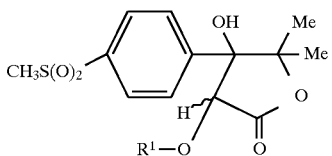

which after dehydration in the presence of a water scavenger yields a compound of formula I.

3. A process according to claim 2 wherein the water scavenger is isopropyl trifluoroacetate.

4. A process according to claim 2 wherein the aprotic solvent is acetonitrile.

5. A process according to claim 2 wherein the strong base is 1,8-Diazabicyclo[5.4.0]undec-7-ene.

6. A process according to claim 2 wherein the water scavenger is isopropyl trifluoroacetate; the aprotic solvent is acetonitrile; and the strong base is 1,8-Diazabicyclo[5.4.0]undec-7-ene.

7. A process according to claim 6 wherein R$^1$ is isopropyl.

8. A process according to claim 2 or 7 for making compounds of Formula I comprising the steps of:
(d) reacting compound 4:

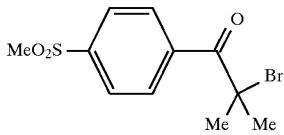

in an alkanol solvent with compound 5:

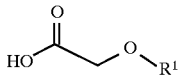

in the presence of a suitable base to yield a compound of formula 6:

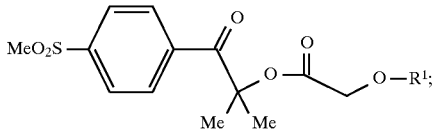

(e) reacting compound 6 in an aprotic solvent with a strong base to yield a cyclized compound of formula 7:

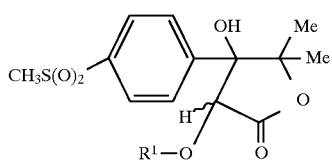

which after dehydration in the presence of a water scavenger yields a compound of formula I.

9. A process according to claim 8 for making compounds of Formula I comprising the steps of:

(c) oxidizing compound 3:

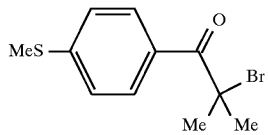

in a non-reactive solvent with an oxidizing agent, optionally in the presence of a suitable catalyst to yield compound 4:

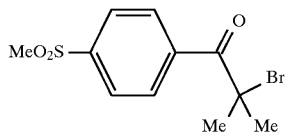

(d) reacting compound 4 in an alkanol solvent with compound 5:

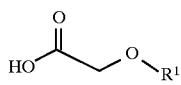

in the presence of a suitable base to yield a compound of formula 6:

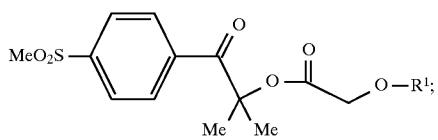

(e) reacting compound 6 in an aprotic solvent with a strong base to yield a cyclized compound of formula 7:

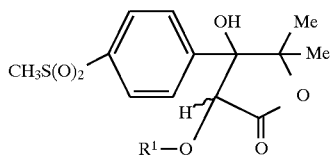

which after dehydration in the presence of a water scavenger yields a compound of formula I.

10. A process according to claim 9 for making a compound of formula I comprising the steps of:

(b) brominating compound 2:

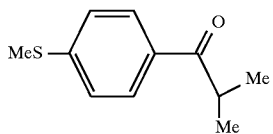

with a brominating agent in a non-reactive solvent, in the presence of a second solvent to yield compound 3:

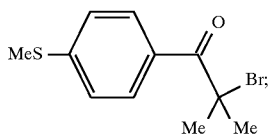

(c) oxidizing compound 3 in a non-reactive solvent with an oxidizing agent, optionally in the presence of a suitable catalyst to yield compound 4:

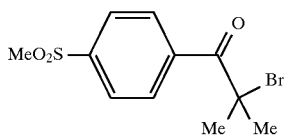

(d) reacting compound 4 in an alkanol solvent with compound 5:

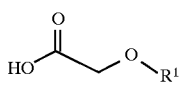

in the presence of a suitable base to yield a compound of formula 6:

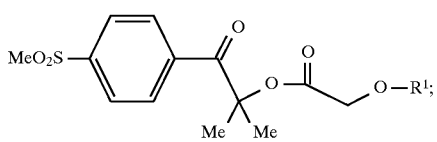

(e) reacting compound 6 in an aprotic solvent with a strong base to yield a cyclized compound of formula 7:

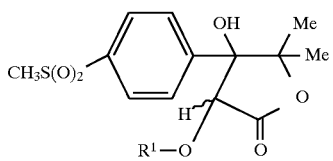

which after dehydration in the presence of a water scavenger yields a compound of formula I.

* * * * *